United States Patent [19]

Karady et al.

[11] Patent Number: 4,869,791

[45] Date of Patent: Sep. 26, 1989

[54] PROCESS FOR PREPARING 10,11-DIHYDRO-11-EXO-HYDROXY-5-METHYLDIBENZO[A,D]CYCLOHEPTEN-5,10-IMINE

[75] Inventors: Sandor Karady, Mountainside; Leonard M. Weinstock, Belle Mead, both of N.J.

[73] Assignee: Merck & Co., Inc., Rahway, N.J.

[21] Appl. No.: 211,210

[22] Filed: Jun. 24, 1988

[51] Int. Cl.$^4$ .................................... C25B 3/00
[52] U.S. Cl. ............................ 204/72; 204/73 R; 204/78; 204/59 R
[58] Field of Search ............... 204/59 R, 72, 73 A, 204/73 R, 78, 74

[56] References Cited

U.S. PATENT DOCUMENTS 4,399,141  8/1983  Anderson et al. ............. 424/256

FOREIGN PATENT DOCUMENTS 0264183  4/1988  European Pat. Off. .

OTHER PUBLICATIONS

Baizer et al., "Organic Electrochemistry", 2nd ed., Marcel Dekker Inc., New York, pp. 534–541, (1983).

*Primary Examiner*—John F. Niebling
*Assistant Examiner*—Steven P. Marquis
*Attorney, Agent, or Firm*—William H. Nicholson; Joseph F. DiPrima

[57] ABSTRACT

10,11 Dihydro-11-exo-hydroxy-5-methyldibenzo[a,d]cyclohepten-5,10-imine is prepared in a four step synthesis which uses an electrochemical cyclization to form the 5,10-imine bridge in about a 50% yield.

6 Claims, No Drawings

PROCESS FOR PREPARING 10,11-DIHYDRO-11-EXO-HYDROXY-5-METHYL-DIBENZO[A,D]CYCLOHEPTEN-5,10-IMINE

SUMMARY OF THE INVENTION

This invention is concerned with a novel process for the synthesis of 10,11-dihydro-11-exohydroxy-5-methyldibenzo[a,d]cyclohepten-5,10-imine a potent N-methyl-D-aspartate antagonist useful as an anticonvulsant and in the prevention and treatment of disease states resulting from cerebral neurodegeneration such as in Alzheimer's disease.

The key step in the synthesis is an electrochemical cyclization forming the 5,10-imine bridge which is depicted as follows:

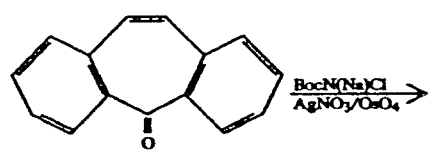

BACKGROUND OF THE INVENTION 10,11-Dihydro-5-methyldibenzo[a,d]cyclohepten-5,10-imine, also known as MK-801 is a potent anticonvulsant and is the subject of U.S. Pat. No. 4,399,141 by Anderson et al.

The 11-exo-hydroxy derivative of MK-801 has been shown to be a major mammalian metabolite of MK-801 and both compounds have been shown to be N-methyl-D-aspartate (NMDA) antagonists useful in the treatment of neurodegenerative diseases such as Alzheimer's disease and related neurological disorders as described by Britcher et al., in European patent publication No. 0264183.

The synthetic route disclosed in the prior art for the synthesis of 11-exo-hydroxy-MK-801 is very inefficient with an overall yield of about 11% to racemic product.

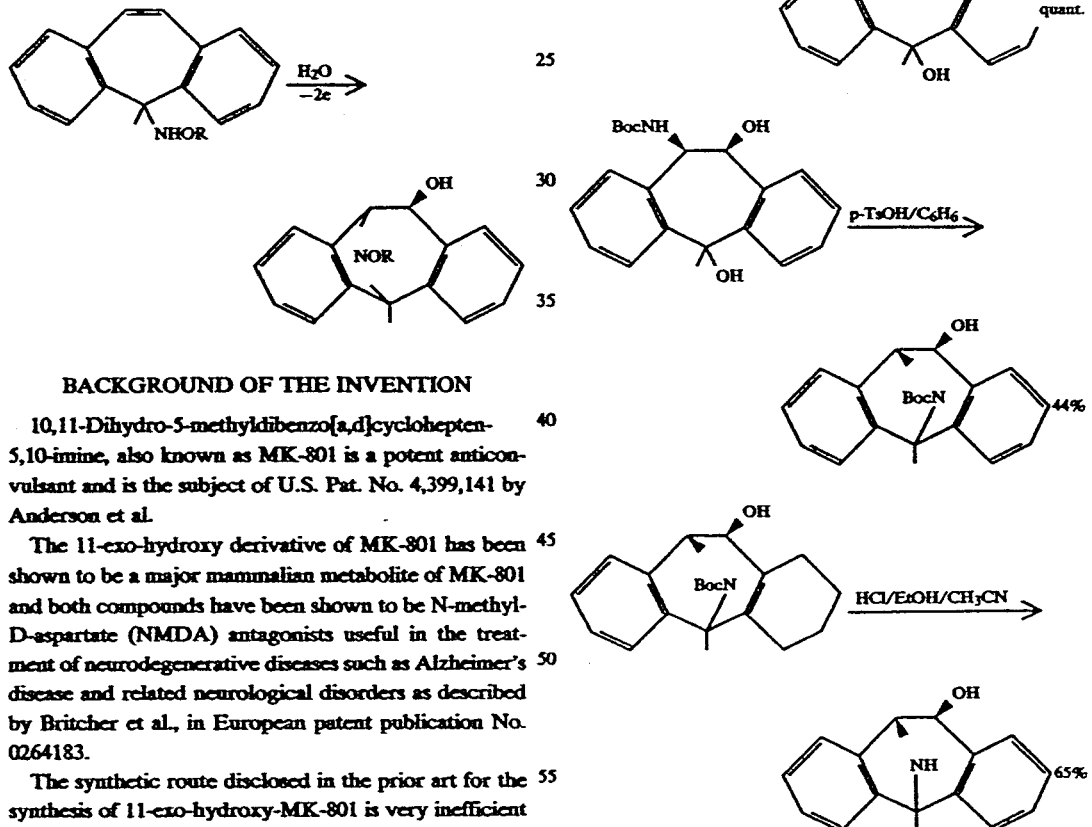

Now with present invention, there is provided a new process for preparing racemic 11-exo-hydroxy-MK-801 in about 50% overall yield.

DETAILED DESCRIPTION OF THE INVENTION

The novel process of this invention is depicted as follows:

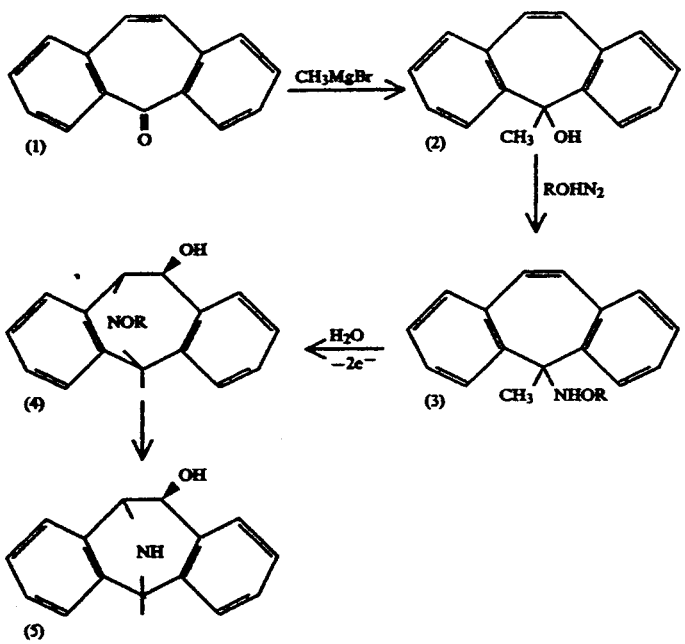

EXAMPLE 1

(±)-10,11-Dihydro-11-exo-hydroxy-5-methyldibenzo[a,d]cycloheptene-5,10-imine(5)

Step A:

Preparation of 5-Methyl-5-Methoxylamino-5H-dibenzo[a,d]cycloheptene(3)

Compound 1 is a well known commercially available starting material useful in the synthesis of a number of important medicinal agents such as amitriptyline, cyclobenzaprine, protriptyline and nortriptyline. By a standard Grignard reaction with methyl magnesium bromide there is produced Compound 2.

Treatment of 2 with $RONH_2$ wherein R is $C_{1-3}$ alkyl, $C_{2-4}$ alkanoyl or $C_{2-4}$ alkanoyloxy, and an organic acid of pka about 1-2 such as dichloroacetic acid in an organic solvent such as methylene chloride, chloroform, acetonitrile or mixtures thereof at about 40°-50° C. for about 2 to 6 hours, or until the carbinol, 2, has substantially disappeared, provides 3.

Treatment of 3 in aqueous THF solution in the presence of an electrolyte such as $NaBF_4$, $LiOSO_2CF_3$, $N(C_2H_5)_4BF_4$, or $LiClO_4$ with direct current electrolysis at a voltage of about 1-2 volts and a current density of about 25 to 100 $mA/cm^2$ results in about a 55% yield of 4. The anode in the electrolysis cell can be of various materials such as polycarbon felt, reticulated vitreous carbon, or a simple carbon rod, but preferably a carbon felt designated GSF-6 available from Electrosynthesis Corporation, East Amherst, NY.

The —OR group is removed by reductive cleavage. For example reductive cleavage of the N-methoxy group from 4 is accomplished in refluxing THF by slow addition of an excess of borane-methylsulfide (BMS). The reaction is complete after about 4-5 hours at reflux with downward distillation of dimethyl sulfide.

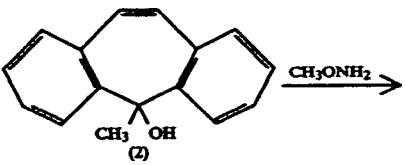

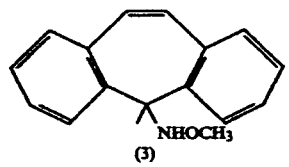

Materials

| | |
|---|---|
| N—Methoxylamine HCl | 65 g, 0.78 M |
| Sodium Acetate, Fused, Anhydrous | 63.8 g, 0.78 M |
| Dichloroacetic acid | 100.4 g, 0.78 M |
| Carbinol 2 | 86.5 g, 0.39 M |
| Methylene chloride Sieve Dried (KF = 8 μg/ml) | 930 ml |
| Acetonitrile, Sieve Dried (KF = 9 μg/ml) | 235 ml |
| Ammonium Hydroxide - 15% | 870 ml |
| Brine | 400 ml |
| Hexane | 1.8 l |

A 3 liter flask containing methylene chloride (500 ml), acetonitrile (200 ml), methoxylamine hydrochloride (65 g=0.78M) was purged three times with nitrogen. Using an ice bath to maintain a temperature of 15°-20° C., dichloracetic acid (100.4 g, 64 ml, 0.78M) was added over 15-30 minutes.

The reaction was then heated to 45° C., aged for ½ hr, and cooled to 20° C. The carbinol, (86.5 g–0.39M) dissolved in methylene chloride (340 ml) and acetonitrile (35 ml) was then added to the flask (below 25° C.) over a period of approximately 10 minutes. The mixture was heated to 45°-47° C. for 3 hrs, until carbinol content was reduced to <1 area %.

LC conditions: 70:30:01.1 CH₃CN:H₂O:H₃PO₄.

Flow 1 ml/min, 210. S.M.: 5 min; prod: 6.16 min on a Zorvax C8 reverse phase column.

After cooling the mixture to 15° C., 15% ammonium hydroxide solution (870 ml) was added over a period of 30 minutes, while keeping the temperature below 20° C. The reaction mixture was stirred for an hour, the layers were separated and the organic layer washed with brine (400 ml). The filtered solution was concentrated on a Buchi evaporator to about 400 mL The concentrate was diluted with 450 ml of hexane and reconcentrated. The hexane flush was repeated.

The residue was reslurried in 450 ml of hexane, cooled to 0°-5° C., aged for 2 hrs and the product was removed by filtration. The cake was washed with cold hexane (350 ml) and dried to constant weight at room temperature under house vacuum. White, crystalline, methoxylamino compound was obtained: 88.9 g, 90.9% yield.

M.P.=130°-132° C.

L.C. (70/30/0.1=CH₃CN:H₂O:H₃PO₄) C8 Zorbax reverse phase column

Product (6.2 min)=99.07%
S.M. (5 min)=0.0%
Tetraene (8.1 min)=0.08%

Step B:

Preparation of
11-hydroxy-5-Methyl-12-Methoxy-10,11-dihydro-5H-dibenzo[a,d]cyclohepten-5,10-imine(11-Hydroxy-N-Methoxy-MK-801)4

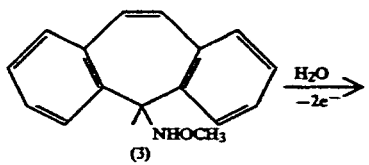

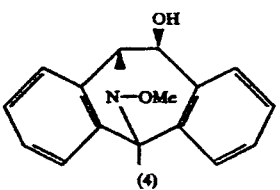

Materials

| N—Methoxyamino Compound 3 | 75 g, 0.3 M |
| Sodium Tetrafluoroborate | 18 g, 0.16 M |
| THF | 950 ml |

-continued

| Water | 600 ml |
| Methylene Chloride | 500 ml |
| Sat. Sodium Bicarbonate solution | 200 ml |
| Brine | 100 ml |

A 2 liter resin kettle was fitted with a 50 cm² carbon felt (5×10 cm) anode, a stainless steel (100 cm²) cathode, a mechanical stirrer, thermometer and N₂ inlet. Into this reaction vessel was added THF (950 ml) and methoxylamine 3 (75 g, 0.3 Moles). After dissolution, a solution of sodium tetrafluoroborate (18 g–0.17M) in water (400 ml) was added. The power was then turned on and held at a constant current of 4 Amps, (28–30 volts) for 6 hours until the LC analysis for starting material was below 1%.

LC conditions: 40:60:0.1 CH₃CN:H₂O:H₃PO₄, C8 Zorbax reverse phase column. λ230, 2 ml/min SM 12.14 min, Prod. 5.46 min. Response factor 5:1 for SM: Prod (compounds 3:4).

The reaction was then filtered, and the electrodes were washed with THF, and the solution was concentrated on a rotary evaporator.

Saturated sodium bicarbonate solution was added (200 ml, pH=7.5) and the mixture was extracted with methylene chloride (200 ml and 2×100 ml). The combined organic layers was washed with water (200 ml) and brine (100 ml), dried over magnesium sulfate, filtered and concentrated to a foam (83.63 g, 104.8% of theory).

For assay, the dried methylene cloride solution was mixed with a standard 2,4-dibutyl phenol solution and the mixture was evaporated to dryness. H¹ NMR assay in CDCl₃ is based on comparing the integrals of tBu with that of the sum of the syn and anti O—C—H or —N—C—H signals.

LC (uncorrected area %): Product 4+8=55.4%, SM. (3)=2.24%.

In similar electrolyses wherein OR, the nitrogen substituent, is acetoxy and t-butyoxycarbonyloxy yields of 70% were realized.

Step C

Preparation of
(±)-10,11-Dihydro-11-exohydroxy-5-methyl-dibenzo[a,d]cycloheptene-5,10-imine (5).

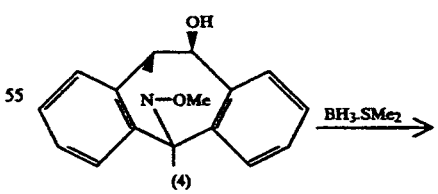

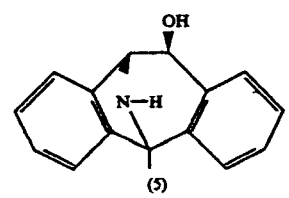

Materials

| | |
|---|---|
| Methoxylamine 4 (crude) | 103.6 gm |
| Borane-methylsulfide complex (10 M) | 116 ml, 1.16 mole |
| Tetrahydrofuran | 600 ml |
| Methanol | 500 ml |
| 6 M Sulfuric acid | 225 ml |
| Acetonitrile | 1600 ml |
| 50% NaOH | 125 ml |

To a 2 liter 3-necked flask equipped with overhead stirrer, reflux condenser, addition funnel and nitrogen purge, was charged the methoxylamine (4) (103.6 g) and 600 L tetrahydrofuran. The solution was heated to reflux and borane-methylsulfide (116 ml, 1.16 mole) was added, dropwise, to the refluxing solution.

When the addition was complete the cooling water to the condenser was turned off and the top of the condenser was fitted with a distillation head and condenser. Dimethyl sulfide is collected along with some tetrahydrofuran.

If the dimethylsulfide is not distilled off as the reaction proceeds, the reaction time is greatly increased.

The reaction was followed by HPLC and was complete after 4 hours.

HPLC conditions 40:60 CH$_3$CN/0.1% aqueous H$_3$PO$_4$.Altex C$_8$, 230 nm, 2 ml/min
4 6.20 min
5 5.30 min
9 4.86 min (endo-hydroxy)

Aliquots were quenched into 6N H$_2$SO$_4$/methanol solution and boiled for 30 seconds. An aliquot of this solution was then diluted with acetonitrile/aqueous H$_3$PO$_4$ and assayed. Reaction was considered complete when 4 was less than 1 area %.

The solution was cooled to <30° C. and transferred to an addition funnel (reaction volume ~500 ml). The reaction vessel was then charged with a solution consisting of 50 ml methanol and 225 ml 6M H$_2$SO$_4$. The reaction solution was added to the acidic methanol solution over 20 minutes. After this, the solution was heated at reflux for 20 minutes then the condenser was replaced with a distillation head and ca. 250 ml solvent was collected. The solution was then cooled to 20°-25° C. and the remaining organic solvents were removed in vacuo on a rotary evaporator.

The remaining aqueous slurry was cautiously treated with 50% sodium hydroxide (125 ml) until the mixture is strongly basic (pH>11).

The slurry was diluted with 500 ml water, cooled to 15° C. and then filtered. The cake was washed with 2×200 ml water then sucked dry under nitrogen sweep overnight.

The dried cake was dissolved in 1500 ml refluxing acetonitrile. The hot solution was filtered to remove insoluble matter (6.0 gm). The filtrate was allowed to cool, stirred at 0° C. for 1 hour. The crystalline product was filtered off and the cake was washed with 100 mL cold acetonitrile. The product was dried in vacuo at 40° C. under nitrogen bleed to a weight of 34.51 g.

The mother liquors were concentrated to ca. ⅓ volume to produce 5.34 g as a second crop. Further concentration of the mother liquors produced a third crop of 6.42 g.

The final mother liquors were assayed by HPLC and found to contain approximately 3.0 g of product.

Total isolated yield 46.27 m.

(91% yield, based on 55% purity for crude 4).

HPLC

1st crop 99.14 area % 5; 0.86 area % endo isomer (9)

2nd crop 97.61 area % 5; 2.39 area % endo isomer (9)

3rd crop 91.82 area % 5; 4.47 area % endo isomer (9)

The three crops from this run and from a previous reduction of 75 gms crude 4 were combined (75.3 g total weight) in 500 ml acetonitrile and refluxed for one hour under N$_2$. The mixture was cooled, then stirred at ice bath temperature for 1.5 hrs. The solids were then filtered and the cake was washed with 100 mL cold acetonitrile. After drying overnight at 38° C. in vacuo (27 in. Hg) with N$_2$ bleed 71.75 gm 5 was obtained as an ivory colored crystalline solid. Mp 213°-216.5° C. A recrystallized sample (12630-112), which gave satisfactory elemental analysis had a melting point of 215°-218° C.

LC 98.2 wt % vs standard 99.2 area % 5 0.8 area % endo-isomer (9)

What is claimed is:

1. A process for the preparation of 10,11-dihydro-11-exo-hydroxy-5-methyldibenzo[a,d]cyclohepten-5-10-imine comprising the electrolysis of a compound of structure:

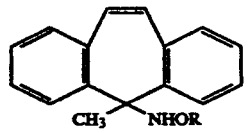

wherein R is a C$_{1-3}$alkyl, C$_{2-4}$alkanoyl or C$_{2-4}$alkoxycarbonyl in the presence of an electrolyte to produce the compound of structure:

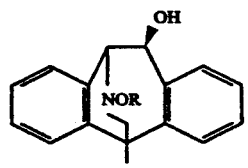

followed by reductive cleavage of the N—OR group.

2. The process of claim 1 wherein R is methyl.

3. The process of claim 2 wherein the electrolysis is conducted with a current density of 25 to 100 mA/cm$^2$.

4. A process of the preparation of a compound of structural formula:

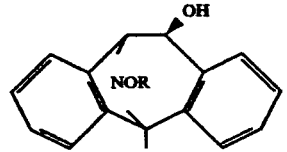

which comprises the electrolysis of a compound of structural formula:

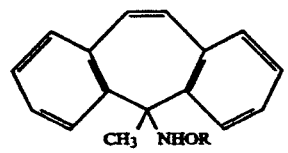

wherein R is C$_{1-3}$alkyl, C$_{2-4}$alkanoyl or C$_{2-4}$alkoxycarbonyl in the presence of an electrolyte.

5. The process of claim 4 wherein R is methyl.

6. The process of claim 4, wherein the electrolysis is conducted with a current density of 25 to 100 mA/cm$^2$.

* * * * *